United States Patent [19]
Henry

[11] Patent Number: 5,875,533
[45] Date of Patent: Mar. 2, 1999

[54] SCALPEL BLADE REMOVER

[75] Inventor: Robert Anthony Neville Henry, Kenmore, Australia

[73] Assignee: Qlicksmart Pty Ltd., Queensland, Australia

[21] Appl. No.: 737,071

[22] PCT Filed: Sep. 8, 1995

[86] PCT No.: PCT/AU95/00585

§ 371 Date: Oct. 29, 1996

§ 102(e) Date: Oct. 29, 1996

[87] PCT Pub. No.: WO96/07363

PCT Pub. Date: Mar. 14, 1996

[30]    Foreign Application Priority Data

Sep. 9, 1994  [AU]  Australia ................................ PM7980

[51] Int. Cl.⁶ ........................................................ B23P 19/02
[52] U.S. Cl. ................................ 29/239; 29/278; 29/270; 206/355
[58] Field of Search .............................. 29/239, 238, 240, 29/243.56, 243.5, 278, 270; 206/355

[56]              References Cited

U.S. PATENT DOCUMENTS

| | | | |
|---|---|---|---|
| 4,106,620 | 8/1978 | Brimmer et al. . | |
| 4,168,777 | 9/1979 | Gaskell et al. ............................ | 29/239 |
| 4,378,624 | 4/1983 | Klingenberg .............................. | 29/267 |
| 4,386,457 | 6/1983 | Coombs .................................... | 29/270 |
| 5,035,703 | 7/1991 | Baskas . | |
| 5,088,173 | 2/1992 | Kromer et al. .......................... | 206/355 |
| 5,163,553 | 11/1992 | Cantwell et al. . | |
| 5,361,902 | 11/1994 | Abidin et al. ............................ | 206/355 |
| 5,449,068 | 9/1995 | Gharibian . | |
| 5,699,908 | 12/1997 | Frye et al. ............................... | 206/355 |

FOREIGN PATENT DOCUMENTS

| | | |
|---|---|---|
| 0034949 | 9/1981 | European Pat. Off. . |
| 0569233 | 11/1993 | European Pat. Off. . |
| WO 91/03984 | 4/1991 | WIPO . |

*Primary Examiner*—David A. Scherbel
*Assistant Examiner*—Lee Wilson
*Attorney, Agent, or Firm*—Panitch Schwarze Jacobs & Nadel, P.C.

[57]              ABSTRACT

A scalpel blade remover removes a blade from the tang of a scalpel. The scalpel is inserted in, and withdrawn from, the blade remover along the same substantially straight-line path. The blade remover has a rocker block which pivots about an axis transverse to the insertion path. When the scalpel is inserted into the blade remover, its tang pushes against a contact surface of the rocker block, causing the rocker block to pivot. A pair of legs at the other end of the rocker block apply a transverse force to the heel of the blade on either side of the tang, thereby lifting the heel of the blade off the tang. When the scalpel has been inserted far enough, a pawl drops behind the heel of the blade. The pawl strips the blade from the tang when the scalpel handle is removed. The blade remover is typically mounted in the lid of a sharps container.

12 Claims, 6 Drawing Sheets

SCALPEL BLADE REMOVER

THIS INVENTION relates to a scalpel blade remover. In particular, the invention is directed to a device which enables a blade to be removed from a scalpel in a simple single-handed operation.

BACKGROUND ART

A conventional surgical scalpel comprises a reusable, sterilisable handle having a tang at one end on which a replaceable slotted blade is mounted. The handle is intended to be used repeatedly, but the blade is normally discarded after each instance of use. Some operations may require several blades to be used successively on the same handle, e.g. where the blades become dull or contaminated, or a different style of blade is required at different stages of the operation.

To remove the blade from the handle, the heel portion of the slotted blade must be bent out of its plane (i.e. transversely to the handle), and then moved axially along the tang so that the heel portion rides over the tang thereby releasing the tang from the slot.

Manual removal of the blade can be difficult, particularly when the scalpel is wet. With the ever increasing spread of blood transmitted diseases, the removal is also a dangerous procedure as any accidental injury from the blade can have life-threatening ramifications.

Many devices have been developed in an effort to facilitate the removal of the blade from the scalpel, and to render the removal procedure less dangerous. Examples of such devices can be found in Australian patent application no. 64111/90, European patent publications 34949 and 569233, Soviet patent specification 1648408, German patent specification 3150904, British patent specifications 1596199 and 2033819, and U.S. Pat. Nos. 3,172,316, 3,825,990, 4,106,620, 4,120,397, 4,168,777, 4,180,162, 4,244,094, 4,270,416, 4,318,473, 4,344,532, 4,378,624, 4,386,457, 4,395,807, 4,466,539, 4,730,376, 4,736,844, 4,903,390, 4,998,334, 5,035,703, 5,088,173, 5,163,553, 5,255,422 and 5,361,902. (The disclosures of these documents are incorporated herein by reference).

However, it has been found that most known devices have inherent problems or disadvantages. Some require two-handed operation (e.g. those described in GB 1596199, U.S. Pat. No. 3,825,990, U.S. Pat. No. 244,094, U.S. Pat. No. 4,378,624, U.S. Pat. No. 730,376, U.S. Pat. No. 4,903,390, U.S. Pat. No. 5,088,173 and U.S. Pat. No. 5,163,553). Other devices require the user to bend, pivot or flex the scalpel handle to cause the blade to be dismounted (e.g. U.S. Pat. No. 1,648,408, U.S. Pat. No. 4,168,777, U.S. Pat. No. 4,270,416, U.S. Pat. No. 4,466,539, U.S. Pat. No. 4,736,844, U.S. Pat. No. 4,746,016 and U.S. Pat. No. 5,035,703). If the handle is not manoeuvred correctly, the blade may not be dislodged. The need to bend the handle in a predetermined, and sometimes complex, movement is frustrating for the surgeon or other user who is typically preoccupied with an operation in progress.

Other devices have a static formation which flexes the blade relative to the handle so that the blade is removed from the tang when the handle is withdrawn (e.g. EP 34949 and GB 2033819). However, in such devices, the handle must be inserted with sufficient force to overcome the resistance caused by the flexing of the blade, and the devices are otherwise awkward to use. Further, some of the known devices are suitable only for particular types of scalpel handles.

European patent publication 569233 describes a scalpel blade remover in which the scalpel is inserted vertically. A bifurcated ramp inside the device causes the scalpel handle to move sideways so that the blade is dislodged from the handle by abutting against the edge of the ramp. However, the successful operation of this device requires that the scalpel handle be held firmly in a vertical direction while it is pushed down by the user, and moved laterally along the ramp, thereby requiring careful and accurate control of the scalpel handle.

It is an object of the present invention to provide a scalpel blade remover which overcomes or ameliorates one or more of the abovedescribed disadvantages, or which at least provides the consumer with a useful choice.

It is a further object of the invention to provide a scalpel blade remover which permits simple, safe and reliable one-handed operation.

SUMMARY OF THE INVENTION

In one broad form, the present invention provides a scalpel blade remover for removing a blade from a tang of a scalpel, comprising a formation permitting the scalpel to be inserted and removed from the blade remover in a substantially straight-line path, a mechanism which is actuated by the forward movement of the tang in the blade remover, to lift the heel of the blade off the tang, and a blade stop member which abuts against the lifted heel of the blade after the blade has travelled past the stop member, whereby upon withdrawal of the scalpel, the stop member prevents rearward movement of the blade and causes the blade to be disengaged from the tang.

The term "heel" is intended to refer to the rear or trailing portion of the blade, having regard to the direction of insertion.

Typically, the formation defines a straight channel along which the scalpel is inserted and withdrawn. The channel may be of open or closed section.

The mechanism for lifting the heel of the blade off the tang suitably comprises a pivotally mounted block having a contact surface at its forward end, i.e. the distal end relative to the user. When the scalpel is inserted, the tang moves along the contact surface in a cam-like manner, causing the block to pivot. The pivoting block is preferably biased against the tang.

The rear end of the pivoting block is bifurcated into a pair of legs which lift the heel of the blade on either side of the tang when the block pivots. In this manner, the heel of the blade is lifted off the tang projection on which it is mounted.

The blade stop member is typically a pawl-like member which drops behind the blade when the blade passes beyond it. When the scalpel is withdrawn from the insertion path, the pawl-like member prevents rearward motion of the blade and causes the blade to be disengaged from the tang.

Alternatively, the blade stop member may be a stepped portion on the end of at least one of the legs.

The scalpel blade remover is suitably mounted on the underside of the lid of a sharps container, with the scalpel path formation extending through an opening in the lid to the outside thereof. The scalpel is inserted from outside the container, but the blade is removed from the scalpel completely within the container.

The sharps container may include means for securely mounting the container to a support surface.

In order that the invention may be more fully understood and put into practice, preferred embodiments thereof will now be described with reference to the accompanying drawings.

DETAILED DESCRIPTIONS OF PREFERRED EMBODIMENTS

Figure 1:
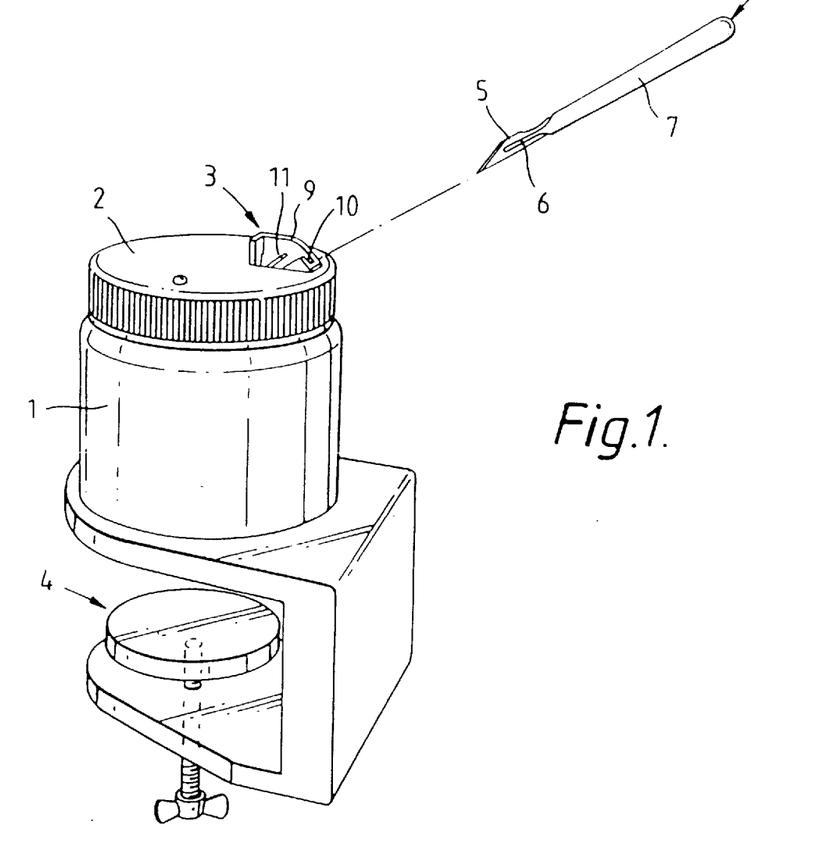
FIG. 1 is a perspective view of a container having a scalpel blade remover according to one embodiment of the invention.

As shown in FIG. 1, a sharps container 1 has a lid 2 in which is mounted a scalpel blade remover 3. The container 1 may suitably have a clamp mechanism 4 on its underside to permit the container to be mounted rigidly to a trolley shelf, ledge or similar. The illustrated container and clamping mechanism are shown by way of example only, and the scalpel blade remover 3 may be fitted to any other suitable container.

The scalpel blade remover 3 is designed to remove a blade 5 from the tang 6 at the forward end of the handle 7 of a scalpel 8. The blade 5 has a slotted aperture, and an elongate boss on the tang 6 is received within that aperture. The leading part of this boss is provided with a peripheral groove which receives part of the slot edge of the blade 5. The construction of the scalpel 8, and the mounting of the blade 5, are well known in the art and need not be described in detail in this application.

The scalpel blade remover 3 is mounted to the underside of the lid 2 of the sharps container 1, and has a guide portion 9 which protrudes through a slot in the lid 2. (Alternatively, the guide portion may be wholly within the container 1). The guide portion 9 of the blade remover 3 defines a substantially straight channel 10 along which the scalpel 8 is inserted. The channel 10 may be an open channel as shown. A guide member 11 may suitably be provided to bias or retain the scalpel in the channel. The scalpel is thereby constrained to move in a straight line path in the channel. (Alternatively, the channel may be a closed section channel with a funnel mouth to facilitate the insertion of the scalpel. The scalpel is simply inserted into the channel, and the channel configuration constrains the scalpel to enter the blade remover 3 in a straight line path).

Figure 2:
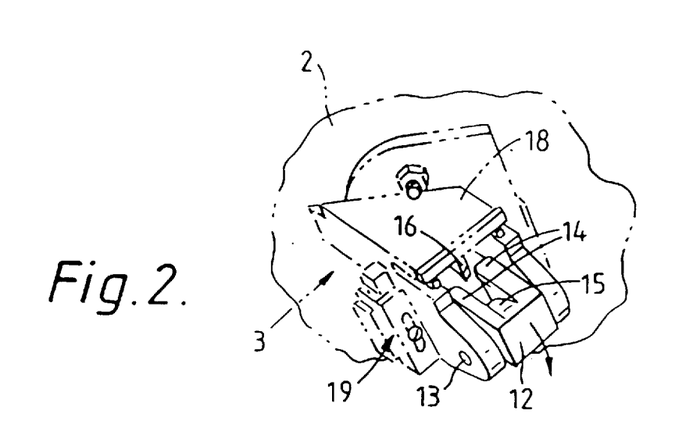
FIG. 2 is a perspective view of the underside of the scalpel blade remover of FIG. 1.

The scalpel blade remover is shown in more detail in FIG. 2. The blade remover comprises a rocker block 12 pivotally mounted on pivot pin 13. (Alternatively, the block 12 may be mounted on a resilient member which permits the block 12 to pivot or rock). The block 12 is lightly biased in a direction opposite to the arrow shown, so that the block 12 may easily pivot in the direction of the arrow against the bias. The bias may be provided by a resilient flap 17 located under the block 12, as shown more clearly in FIGS. 3–6.

The rear end of the block 12 (i.e. the end closest to the opening in the lid) is bifurcated into two legs 14. The forward end of the block 12 has a contact surface 15 between the two legs 14. The contact surface has a cam-like function, as described in more detail below.

A pawl 16 is formed by a flange which depends downwardly from a resiliently mounted flap 18 located opposite, and between, the legs 14 as shown in FIG. 2. The distance between the block 12 and the flap 18 can be varied (if desired) by an adjustable mounting 19.

Typically, the scalpel blade remover is made of moulded plastic components, but other suitable materials may be used.

Figure 3:
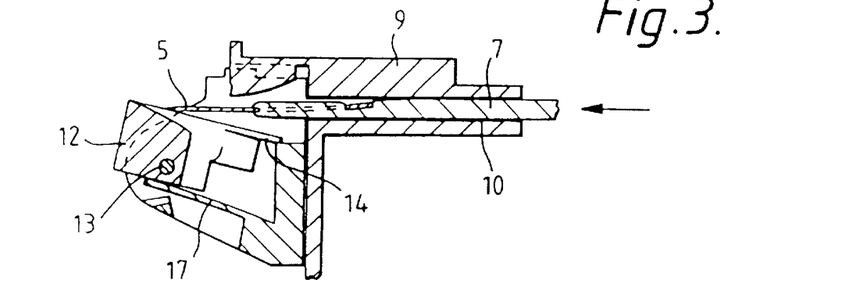
FIGS. 3 to 6 are sectional views of the scalpel blade remover illustrating progressive steps in the blade removal process.
Figure 4:
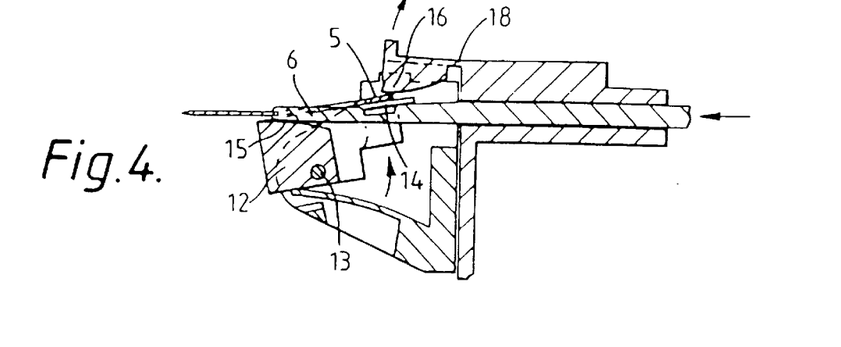

The progressive operation of the scalpel blade remover is illustrated in FIGS. 3 to 6. The scalpel is inserted along the channel 10 in the guide portion 9. The scalpel is inserted until the leading tip of its blade 5 contacts the forward end of block 12 which is biased upwardly by resilient flap 17 (FIG. 3).

As the scalpel is inserted further, the tang 6 abuts the contact surface 15 on block 12. Since the tang is constrained to move only in a straight line path, it causes the rocker block 12 to pivot about pivot pin 13 (in the direction shown by the lower arrow in FIG. 4). As the block 12 pivots, the legs 14 at the rear of the block positively lift the heel of the blade 5 on either side of the tang off the tang boss on which it is mounted. In other words, the longitudinal insertion force is converted, by the rocker block, into a transverse force which lifts the heel of the blade off the boss. The lifting of the blade 5 also lifts pawl 16.

Figure 5:
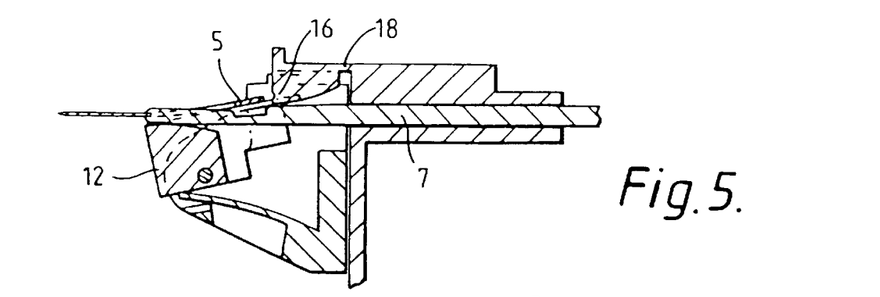

When the scalpel is moved further into the channel 10, the blade clears the pawl 16 which then drops behind the blade 5 under the downward bias of the resilient flap 18 (FIG. 5). The impact of the pawl 16 against the handle 7 of the scalpel creates an audible "click" which indicates to the user that the scalpel has been inserted far enough, and may now be removed.

Figure 6:
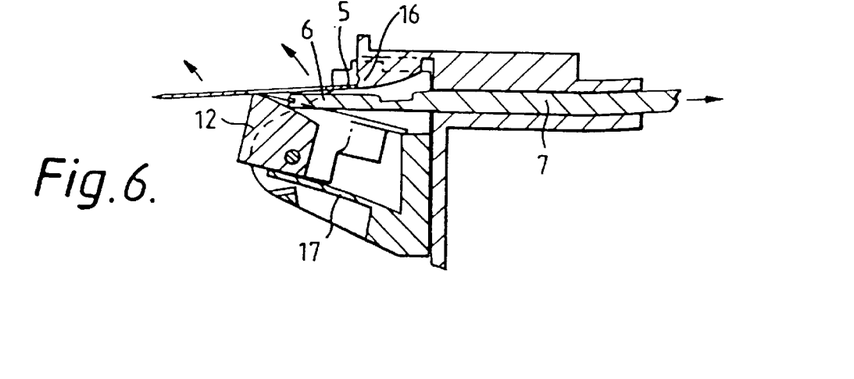

As shown in FIG. 6, when the scalpel is withdrawn along the same path as it was inserted, the rearward movement of the blade 5 is blocked by the pawl 16. The withdrawal of the scalpel therefore removes the tang 6 from the slotted aperture in the blade 5, whereupon the blade 5 falls freely into the sharps container 1. The resilient flap 17 biases the pivoting block 12 back to the initial position shown in FIG. 3.

Figure 7:
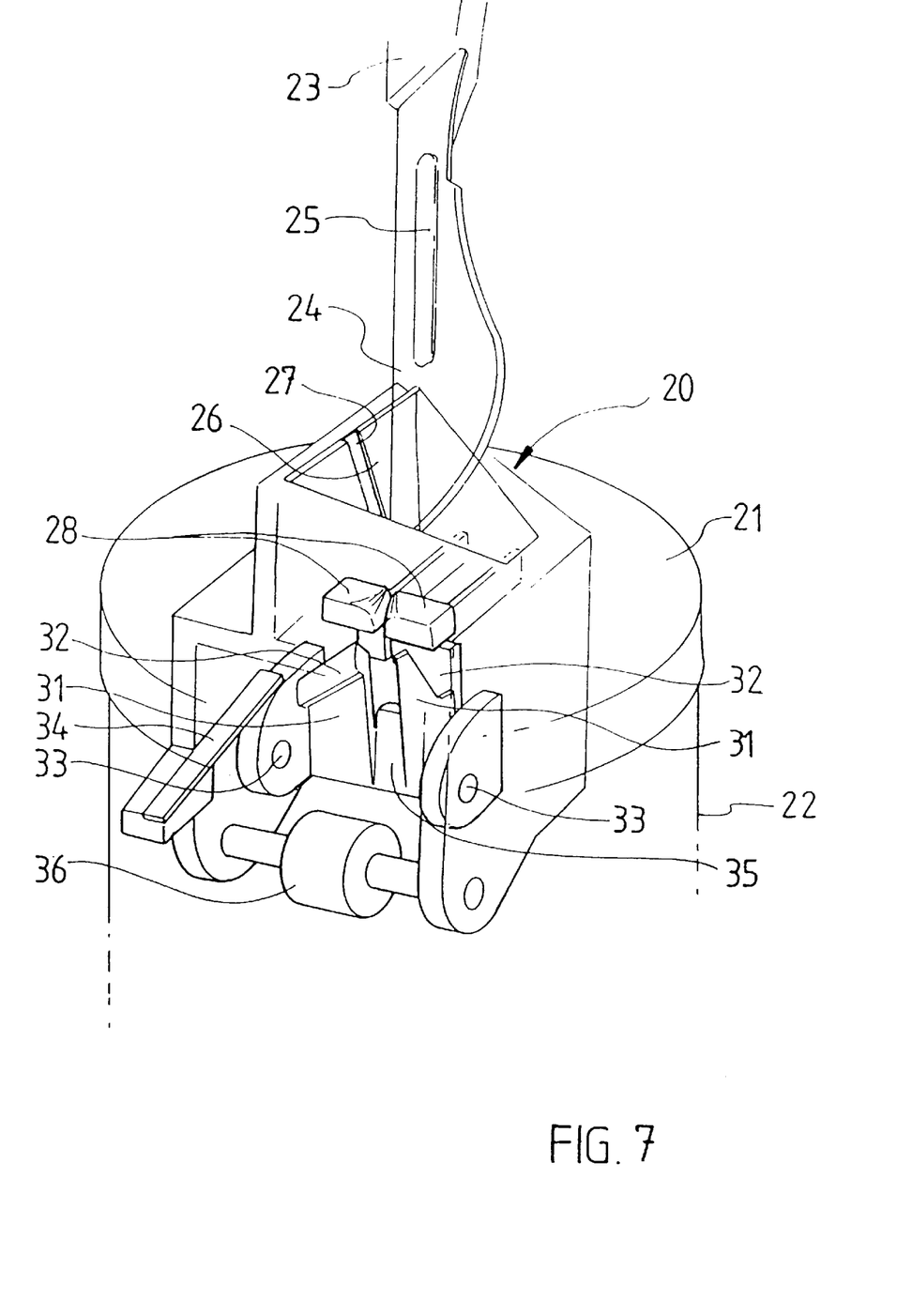
FIG. 7 is a perspective view of a scalpel blade remover according to another embodiment of the invention.

A second embodiment of this invention is shown in FIG. 7. Only the main operating components of the blade remover are shown in FIG. 7, the remaining components being omitted for clarity.

The blade remover 20 of the second embodiment operates according to the same general principle as the blade remover shown in FIGS. 1 and 2. The blade remover 20 is typically fitted to the lid 21 of a sharps container 22 so that the removed blades fall automatically into the container 22.

The blade remover 20 is designed to remove a blade 24 from the boss on the tang 25 of a scalpel handle 23. The blade remover 20 comprises a mouth portion 26 having a channel 27 along which the scalpel 23 is inserted. The mouth 26 leads to a gate formed by a pair of opposed spring-loaded jaws 28 which are displaced apart by the leading tang 25 to accommodate scalpel handles of different width. In this manner, the blade remover 20 can be used not only with conventional scalpels, but also scalpels with wider handles (of the type typically used in plastic surgery).

The blade remover 20 also comprises a rocker block 30 which is pivotally mounted on pivot pins 33. A portion of the block 30 is bifurcated to form a pair of spaced legs 31, the free ends of which each have a raised or stepped portion 32. A web portion between the two legs 31 forms a contact surface 35.

The rocker block 30 is lightly biased to a preferred position by a resilient strip or leaf spring 34. A guide roller 36 is also provided on the blade remover 20, downstream from the rocker block 30. Like the blade remover of FIG. 1 the components of the blade remover 20 can be suitably made from moulded plastic components.

Figure 8:
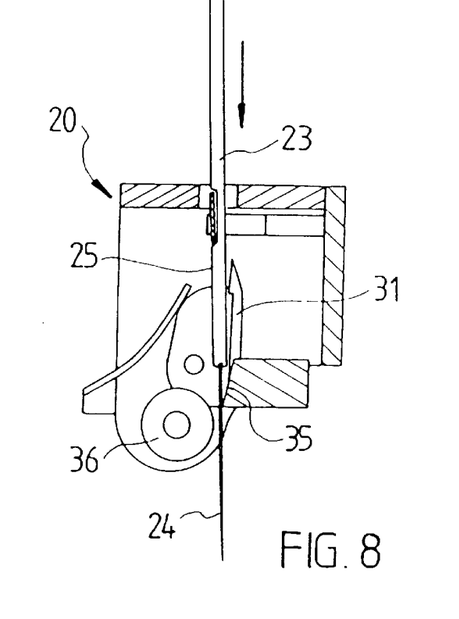
FIGS. 8 to 11 are sectional views of the scalpel blade remover of FIG. 7, illustrating progressive steps in the blade removal process.

The operation of the blade remover 20 is shown schematically in FIGS. 8 to 11. When a scalpel 23 is inserted into the mouth 26 of the blade remover 20, the scalpel is guided by channel 27 in a substantially straight line path. The blade 24 passes over the spring loaded jaws 28 which are pushed apart by the tang 25 of the scalpel handle. The blade 24 passes between the rocker block 30 and the guide roller 36, as shown in FIG. 8. (The curved surface of the roller 36 serves to guide the blade 28 to the right thereof as depicted in FIG. 8).

Figure 9:
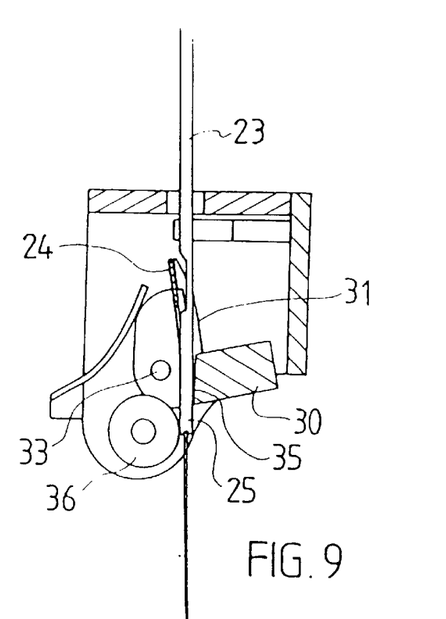

When the tang 25 abuts and passes over the contact surface 35, it imparts a moment to the rocker block 30 about its pivot axis, causing the rocker block 30 to pivot in an anticlockwise direction as shown in FIG. 9. This pivoting motion of the block 30 causes the legs 31 to apply a transverse force to the heel of the blade 24 on either side of the tang 25, thereby lifting the heel of the blade 24 off the tang boss.

Figure 10:
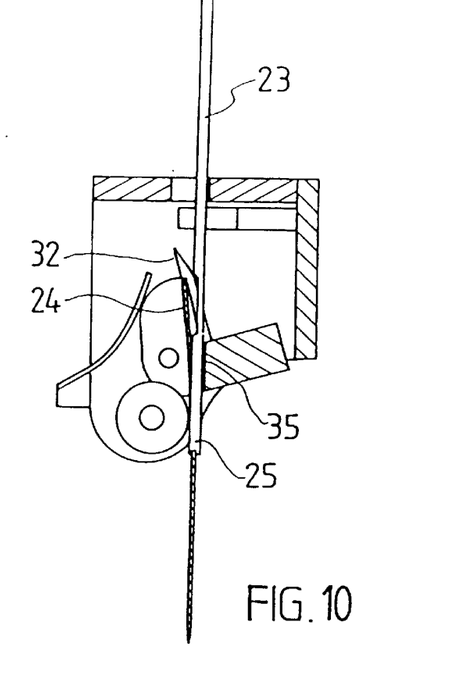

Upon further insertion of the scalpel 23 into the blade remover 20, the heel of the blade 24 slides over the stepped end portions 32 of the legs 31 until the blade clears the stepped portions and drops down onto the lower flat surfaces of the legs 31. This produces an audible "click", thereby indicating to the user that the scalpel has been inserted the required distance, and may then be withdrawn along the same straight-line path.

Figure 11:
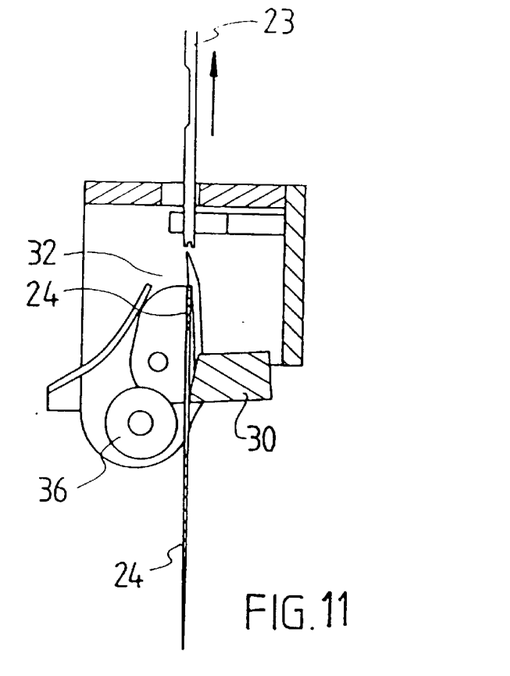

When the scalpel 23 is withdrawn, the rearward motion of the blade is obstructed by the riser surface of the stepped portions 32. As the heel of the blade is still lifted off the boss, and as withdrawal of the blade is prevented, the stepped portions 32 strip the blade 24 from the boss on tang 25 when the scalpel handle 23 is withdrawn (FIG. 11). The removed blade falls freely under gravity into the container below.

The abovedescribed scalpel blade removers have several advantages, including:

(i) The removal of the blade requires only single handed operation. The user simply inserts the scalpel into the blade remover, and withdraws it with one hand. This eliminates the risk of accidentally stabbing a hand holding the device.

(ii) Blade removal requires only a straight-line in-out movement. Thus, the remover is simple to use and, in the case of use by a surgeon or assistant, the blade removal operation does not detract the surgeon's or assistant's attention from the operation in progress.

(iii) The blade is positively lifted off the tang of the scalpel by the pivoting rocker block, thereby ensuring that the blade is always removed.

(iv) The lifting of the blade from the tang does not impede the insertion of the scalpel and hence relatively little insertion force is required.

(v) The user knows when the scalpel has been inserted far enough as this is signalled by the audible "click" of the pawl against the scalpel handle, or blade against the rocker block.

(vi) The blade is removed wholly within the container on which the blade remover is mounted, thereby providing safe disposal of the blade.

(vii) The scalpel blade remover is suitable for use with different types and sizes of handles and blades.

(viii) The scalpel blade remover can be used in both medical and non-medical work places.

(ix) The blade remover can be used as a sterile device in an operating theatre.

Unused scalpel blades are normally provided in a sealed sterile package. At the conclusion of surgery, it is important that all blades used during the surgery be accounted for. In a further embodiment of this invention, illustrated in FIG. 12, a blade remover is incorporated in a small disposable container.

Figure 12:
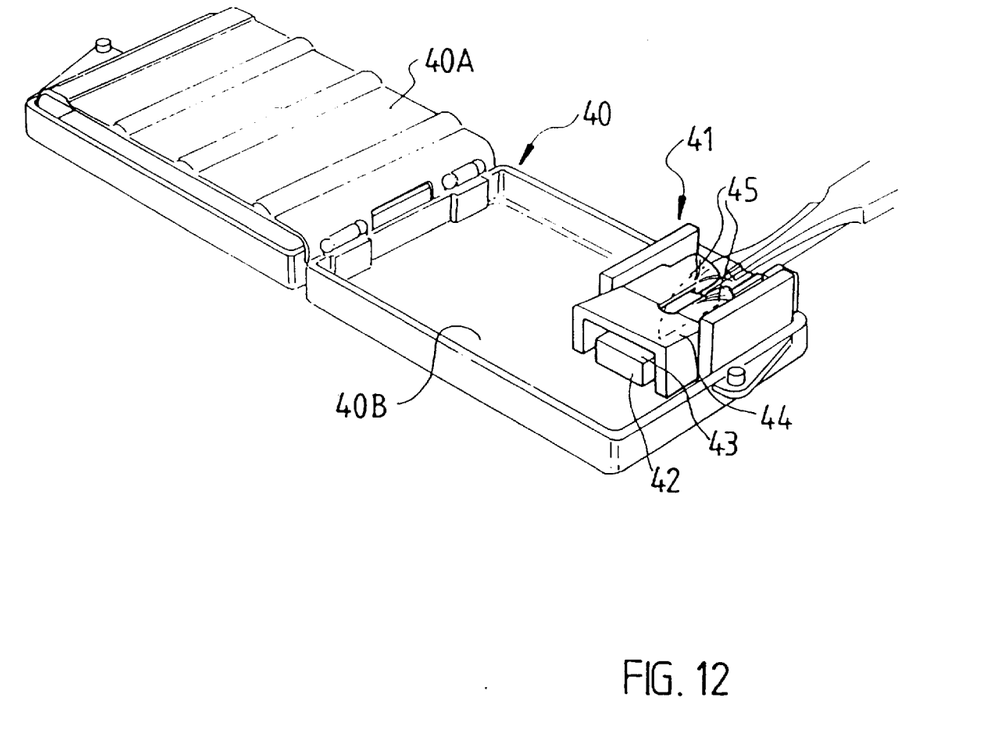
FIG. 12 is a perspective view of a disposable sharps container incorporating a scalpel blade remover according to yet another embodiment of the invention.

As shown in FIG. 12, a container 40 is formed by two hinged portions. A blade remover 41 is mounted in one of the hinged portions. The blade remover and the container 40 may suitably be made of moulded plastic components. The container 40 may also include a foam layer 40A for holding surgical needles and blades, as is known in the art. Alternatively, a magnetic layer 40B may be placed in the container for fixing suture needles and blades. The magnet 40B may be numbered to assist counting of used needles and blades.

The blade remover 41 comprises a fixed block 42 having a contact surface 43. A rocker portion 44 is pivotally mounted above the fixed block 42 and is able to rock back and forth about its pivot axis. On one side of its pivot axis (shown to the left in FIG. 12), the rocker portion 44 has a ramped contact surface 47 on its underside. On the other side of the pivot axis, the rocker portion 44 is bifurcated into two legs 45. The free ends of the legs have stepped portions 46 on their underside, and their top sides are sloped downwardly at the free ends to form tapered inner corners.

Figure 13:
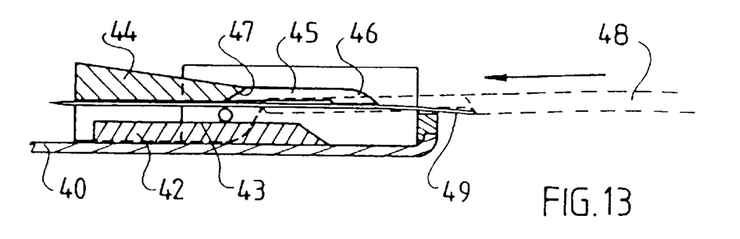
FIGS. 13 to 16 are sectional elevational views of the scalpel blade remover of FIG. 13, illustrating progressive steps in the blade removal process.
Figure 14:
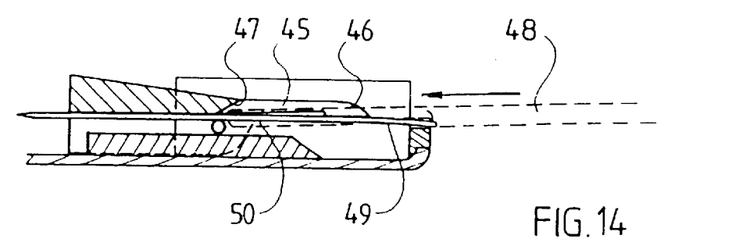

The operation of the blade remover is illustrated in FIGS. 13 to 16. The blade remover 41 operates on the same principle as the blade removers of FIGS. 2 and 7. Holding the scalpel handle 48, the user inserts the blade end of the scalpel into the blade remover 41 in a substantially straight line path. If the blade remover is orientated generally horizontal as shown in FIG. 12, the scalpel is inserted with the blade on its lower side. The blade 49 is inserted between the rocker portion 44 and the fixed block 42. The tang 50, on which the blade is mounted, passes between the legs 45 of the rocker portion 44 (FIG. 13).

Preferably, the side of the rocker portion 44 having the contact surface 47 is weighted more than the other side having the legs 44, so that in its rest position, the legs 45 are raised slightly to form a mouth therebelow for receiving the bladed scalpel.

As the tang 50 passes between the legs 45, the inner tapered corners at the ends of the legs wedge between the blade and the scalpel handle. When the tang 50 is inserted further between the fixed block 42 and the ramped contact surface 47 of rocker portion 44, the rocker portion 44 pivots about its axis (in a clockwise manner when viewed as in FIG. 14). The pivoting of the rocker portion 44 causes the legs 45 to impart a force on the heel of the blade 49 on either side of the tang, transversely to the longitudinal axis of the scalpel 48, to lift the heel of the blade 49 off the tang.

Figure 15:
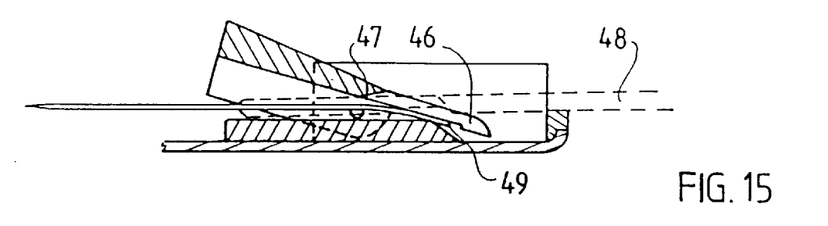

As the scalpel 48 is pushed further into the blade remover 41, the blade 49 rides over the stepped portions 46 on the ends of legs 44, until the rear end of the blade 49 clears the stepped portions 46 (FIG. 15). Due to the resilient nature of the blade, it gives an audible "click" as it steps from the end portions 46 to the intermediate portion of the legs 45. This indicates that the scalpel 48 has been inserted the required distance.

Figure 16:
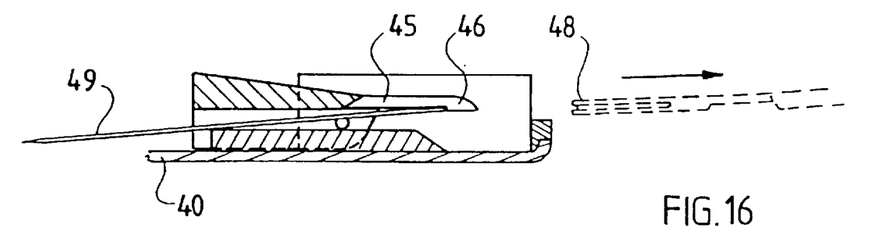

The scalpel 48 may then be withdrawn along the same straight line path (FIG. 16). The riser face of each stepped portion 46 obstructs the rearward movement of the blade 49. Thus, as the scalpel handle 48 is withdrawn, the stepped portions 46 strip the blade 49 from the tang 50.

The loose blade is automatically received within the container half in which the blade remover 41 is located. After all the used blades have been removed and counted, the container 40 is simply closed and disposed.

The foregoing describes only some embodiments of the invention, and modifications which are obvious to those skilled in the art may be made thereto without departing from the scope of the invention. For example, the pivoting block 12 may be replaced by a linkage mechanism which lifts the blade from the tang in response to the forward movement of the tang.

I claim:

1. A scalpel blade remover for removing a blade having a heel from a tang of a scalpel, comprising;
    a structure having a channel permitting the scalpel to be inserted and removed from the blade remover in a substantially straight-line path,
    a mechanism which is moved by forward movement of the tang into the blade remover to thereby cause the mechanism to positively lift the heel of the blade off of the tang with a lifting force dependent upon the extent of the forward motion of the tang, and
    a blade stop member which abuts against the lifted heel of the blade after the blade has traveled past the stop member, whereby upon withdrawal of the scalpel, the stop member prevents rearward movement of the blade and causes the blade to be disengaged from the tang.

2. A blade remover as claimed in claim 1, wherein the mechanism comprises a moveable member having first and second portions, the moveable member being positioned such that the first portion is contacted by the tang when the tang is operatively inserted into the blade remover, the moveable member being moved by the physical urging of the tang against the first portion, and wherein such movement of the moveable member causes the second portion thereof to apply a substantially transverse force to the heel of the blade to lift it off the tang.

3. A blade remover as claimed in claim 2, wherein the moveable member is rotatable about an axis transverse to the insertion path.

4. A blade remover as claimed in claim 3, further comprising means to bias the moveable member in one direction about the axis.

5. A blade remover as claimed in claim 2, wherein the second portion comprises a contact surface generally aligned with the tang in the insertion path.

6. A blade remover as claimed in claim 2, wherein the second portion is bifurcated to form a pair of leg members, each located on opposite sides of the tang and in juxtaposition with the blade when the blade is inserted in the blade remover.

7. A blade remover as claimed in claim 6, wherein the blade stop member comprises a stepped portion on the free end of at least one of the leg members.

8. A blade remover as claimed in claim 6, wherein the blade stop member is a pawl located between the leg members and opposed thereto.

9. A blade remover as claimed in claim 8, wherein the pawl is resiliently mounted.

10. A blade remover as claimed in claim 1, wherein the blade remover is mounted to a container lid.

11. A scalpel blade remover for removing a blade having a heel from a tang of a scalpel, comprising:
    means for receiving the tang of the scalpel,
    means for positively lifting the heel of the blade off of the tang, and
    blade stop means for preventing rearward movement of the lifted blade such that the blade is disengaged from the tang upon withdrawal of the scalpel,
    wherein the blade lifting means comprises a mechanism which is moved by forward movement of the tang to thereby cause the mechanism to apply a positive force to the heel of the blade transversely to the forward movement of the tang with a lifting force dependent upon the extent of the forward motion of the tang.

12. A blade remover as claimed in claim 11, wherein the mechanism comprises a rocker block mounted for pivotal movement about a pivot axis transverse to the insertion path, the rocker block being pivotable by the urging of the tang against a contact surface thereof, the rocker block having a lifting portion spaced from the contact surface, the lifting portion applying a transverse force to the heel of the blade when the rocker block is pivoted by the tang.

* * * * *